United States Patent
Moszner et al.

(10) Patent No.: US 9,138,382 B2
(45) Date of Patent: Sep. 22, 2015

(54) USE OF POLYMERIZABLE MACROCYCLIC POLYETHERS AND MACROCYCLIC HETEROANALOGOUS POLYETHERS IN DENTAL MATERIALS

(75) Inventors: Norbert Moszner, Triesen (LI); Frank Zeuner, Schellenberg (LI); Urs Karl Fischer, Arbon (CH); Volker M. Rheinberger, Vaduz (LI); Iris Lamparth, Grabs (DE)

(73) Assignee: Ivoclar Vivadent AG, Schaan (LI)

( * ) Notice: Subject to any disclaimer, the term of this patent is extended or adjusted under 35 U.S.C. 154(b) by 719 days.

(21) Appl. No.: 12/684,308

(22) Filed: Jan. 8, 2010

(65) Prior Publication Data

US 2011/0054066 A1    Mar. 3, 2011

(30) Foreign Application Priority Data

Aug. 25, 2009  (EP) .................... 09168604

(51) Int. Cl.
  *A61K 6/083* (2006.01)
  *A61K 6/00* (2006.01)
  *A61K 6/087* (2006.01)
  *C07D 257/02* (2006.01)
  *C07D 323/00* (2006.01)
  *C07D 327/00* (2006.01)
  *C07D 498/08* (2006.01)

(52) U.S. Cl.
  CPC ............ *A61K 6/0017* (2013.01); *A61K 6/0023* (2013.01); *A61K 6/087* (2013.01); *C07D 257/02* (2013.01); *C07D 323/00* (2013.01); *C07D 327/00* (2013.01); *C07D 498/08* (2013.01); *A61K 6/0073* (2013.01); *A61K 6/083* (2013.01)

(58) Field of Classification Search
  CPC ............................ A61K 6/083; A61K 6/0073
  USPC ........................................................ 523/116
  See application file for complete search history.

(56) References Cited

U.S. PATENT DOCUMENTS

| | | | | |
|---|---|---|---|---|
| 4,224,415 | A * | 9/1980 | Meitzner et al. ............... | 521/38 |
| 4,866,132 | A * | 9/1989 | Obligin et al. ................ | 525/107 |
| 5,334,625 | A * | 8/1994 | Ibsen et al. ................... | 523/115 |
| 6,043,361 | A | 3/2000 | Evans et al. | |
| 6,241,968 | B1 * | 6/2001 | Tournier et al. ............ | 424/9.363 |
| 6,344,556 | B1 | 2/2002 | Evans et al. | |
| 6,479,592 | B2 | 11/2002 | Rheinberger et al. | |
| 6,569,917 | B1 | 5/2003 | Moszner et al. | |
| 7,365,222 | B2 | 4/2008 | Moszner et al. | |
| 2005/0133453 | A1 * | 6/2005 | Woodruff et al. ............. | 210/683 |
| 2006/0063854 | A1 * | 3/2006 | Jin et al. ....................... | 523/115 |
| 2007/0049713 | A1 * | 3/2007 | Salamone et al. ............ | 526/279 |
| 2008/0242761 | A1 * | 10/2008 | Jia et al. ....................... | 523/118 |

FOREIGN PATENT DOCUMENTS

| | | |
|---|---|---|
| CH | 631 344 A5 | 8/1982 |
| JP | 59-166550 A | 9/1984 |
| JP | 62-167773 A | 7/1987 |
| JP | 04-63877 B2 | 10/1992 |
| JP | 2005248137 A | 9/2005 |

OTHER PUBLICATIONS

Kopolow et al., "Poly(vinyl macrocyclic polyethers). Synthesis and Cation Binding Properties," Macromolecules 6 (1):133-142 (1973).
Okahara et al., "Recent Advances in Syntheses of Crown Compounds," in Hiraoka, ed., Studies in Organic Chemistry—Crown Ethers and Analogous Compounds, vol. 45, Amsterdam:Elsevier, pp. 17-35 (1992).
Pedersen et al., "Makrocyclische Polyäther und ihre Komplexe," Angew. Chem 84:16-26 (1972).
Varma et al., "Polysalt Complexes of Poly(crown Ethers) and Sodium Carboxymethylcellulose," J. Polymer Sci. 15:1189-1197 (1977).
Varma et al., "Polysalt Complexes of Poly(vinylbenzo-18-Crown-6) and of Poly(crown Acrylate)s with Polyanions," J Polymer Sci.: Polymer Chem. Edition 17:1573-1581 (1979).
Weber et al., "Crown Ethers," in Gerhartz, eds., Ullmann's Encyclopedia of Industrial Chemistry, vol. A8, 5th Ed., Wiley-VCH, pp. 91-98 (1987).
Ikemura et al., "Design of a New Dental Adhesive—Effect of a Water-Soluble Sodium Acylphosphine Oxide with Crown Ether on Adhesion to Dental Hard Tissues," Dent. Mater. J. 28(3):267-276 (2009).
European Search Report for EP 09168604.8 (Jan. 13, 2010).

* cited by examiner

*Primary Examiner* — Michael Pepitone
(74) *Attorney, Agent, or Firm* — Ann M. Knab; Thad McMurray

(57) ABSTRACT

Radically polymerizable macrocyclic polyethers or macrocyclic heteroanalogous polyethers, preferably crown ethers, heteroanalogous crown ethers and cryptands for use in dental materials is disclosed.

17 Claims, No Drawings

USE OF POLYMERIZABLE MACROCYCLIC POLYETHERS AND MACROCYCLIC HETEROANALOGOUS POLYETHERS IN DENTAL MATERIALS

This application claims the benefit of European Patent Application Serial No. 09168604.8, filed Aug. 25, 2009, which is hereby incorporated by reference in its entirety.

FIELD

The present invention relates to the use of radically polymerizable macrocyclic polyethers and polymerizable macrocyclic heteroanalogous polyethers in dental materials, in particular for the preparation of adhesives, coatings, cements or composites.

BACKGROUND

Curable dental materials based on an organic monomer matrix which can be cured during application by radical polymerization are known. Examples of such dental materials are adhesives, coatings, cements or composites. With all of these materials, a good substrate adhesion, whether to dentine or tooth enamel or to another dental material, is an important property which can, however, be achieved only with difficulty due to the poor compatibility of organic monomers or polymers on the one hand and the substrate, e.g. dentine or tooth enamel, on the other.

Macrocyclic polyethers (crown ethers) and their heteroanalogous compounds (coronands or corands) in which the O atoms are partially or completely substituted by heteroatoms, above all nitrogen and sulphur, and also bicyclic crown ethers (cryptands) are known in the state of the art (e.g. C. J. Pedersen, H. K. Frensdorf, Angew. Chem. 84 (1972) 16). Examples of crown ethers or their heteroanalogous compounds are [15]crown-5, [18]crown-6 or 1,10-diaza-[18]crown-6:

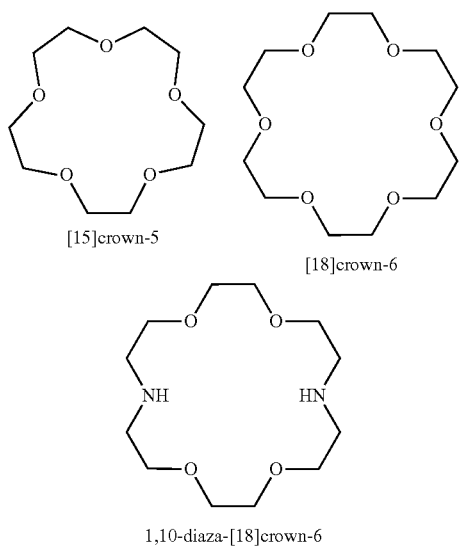

[15]crown-5

[18]crown-6

1,10-diaza-[18]crown-6

In a simplified nomenclature, a crown ether with x ring members and y oxygen atoms is called [x]crown-y (cf. Ullmann's Encyclopedia of Industrial Chemistry, 5th Ed., Vol. A8, 91 et seq.). Additional substituents are placed in front of the name as a prefix, such as e.g. dibenzo[18]crown-6. In the case of bicyclic crown ethers (cryptands), the bridging takes place via two nitrogen atoms, wherein in the designation the number of oxygen atoms of the first, second and third bridges are placed in front of the word cryptand separated by full stops, e.g. [2.2.2]cryptand:

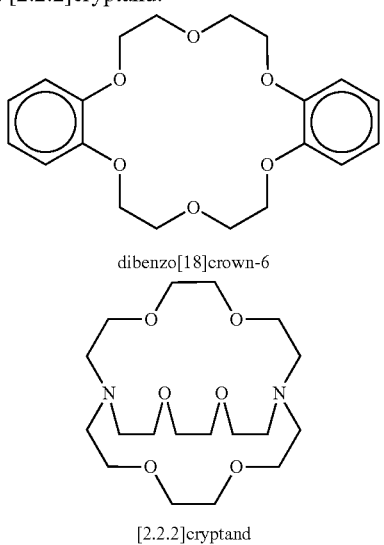

dibenzo[18]crown-6

[2.2.2]cryptand

Polymerizable macrocyclic polyethers, such as e.g. polymerizable crown ethers, are also known. Thus for example ion-binding polymers are obtained by radical polymerization of e.g. 4-vinylbenzo-[15]crown-5 (VB15C5) or 4-vinylbenzo-[18]crown-6 (VB18C6) (S. Kopolow, T. E. Hogen Esch, J. Smid, Macromolecules 6 (1973) 133).

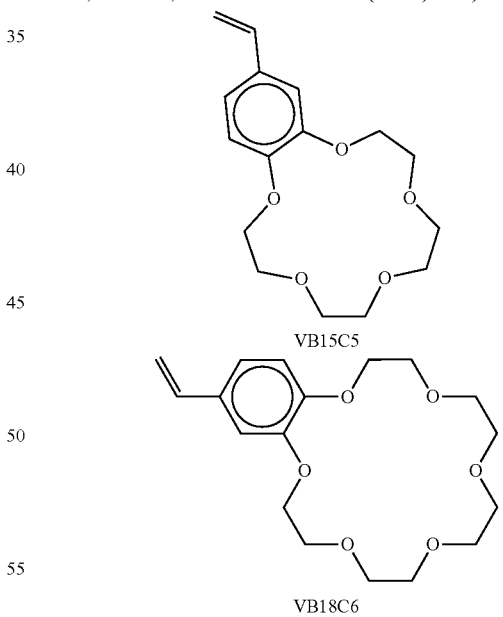

VB15C5

VB18C6

CH-A-631 344 describes a fluoridating composition for dental enamel which, in addition to potassium or sodium fluoride and an organic solvent, such as e.g. acetone, acetonitrile or ethyl acetate, contains a complexing agent, preferably a crown ether (e.g. [18]crown-6) or a cryptand (e.g. [2.2.2]cryptand). The named macrocyclic polyethers are not polymerizable compounds. Rather, the crown ethers used bring about merely a dissolution of the fluoride, accompanied by formation of fluoride ions without a solvation shell. Poorly solvated fluoride ions are said to be absorbed better by the tooth enamel.

SUMMARY

An object of the present invention is to provide novel dental materials with good substrate adhesion, good solubility and good mechanical properties.

The object is achieved by a dental material containing at least 0.05 wt.-%, relative to the total weight of the dental material, of at least one radically polymerizable macrocyclic polyether or radically polymerizable macrocyclic heteroanalogous polyether. The dental material according to the invention preferably contains 0.05 to 40 wt.-%, particularly preferably 1 to 30 wt.-% and quite particularly preferably 1 to 20 wt.-% radically polymerizable macrocyclic polyether and/or macrocyclic heteroanalogous polyether.

The invention further relates to the use of these radically polymerizable macrocyclic polyethers and macrocyclic heteroanalogous polyethers in dental engineering and dentistry, above all for the preparation of adhesives, coating materials, cements and composites for dental purposes.

DETAILED DESCRIPTION

The radically polymerizable macrocyclic polyether or macrocyclic heteroanalogous polyether is a monocyclic or polycyclic, preferably a monocyclic, compound, i.e. a crown ether or heteroanalogous crown ether, or a bicyclic compound, i.e. a cryptand. By heteroanalogous polyethers or heteroanalogous crown ethers is meant within the meaning of this invention polyethers or crown ethers in which the O atoms are partially or completely substituted by other heteroatoms, above all nitrogen and/or sulphur.

In preferred embodiments, the radically polymerizable macrocyclic polyether or macrocyclic heteroanalogous polyether conforms to the general formula MC-(SP-PG)$_n$ (formula I), where MC is a residue, substituted n times,
(a) of a crown ether or heteroanalogous crown ether of the general formula IIa

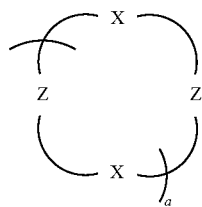

(IIa)

or
(b) of a cryptand of the formula IIb

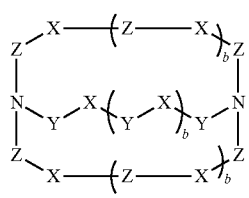

(IIb)

where
X is selected independently of each other in each case from O, S and NR$^1$, wherein R$^1$ stands independently of each other for H, the residue SP-PG or another organic residue;
Y is selected independently of each other from C$_2$-C$_4$ alkylene residues,
Z is selected independently of each other in each case from C$_1$-C$_4$ alkylene, C$_6$-C$_{10}$ arylene and C$_4$-C$_8$ cycloalkylene residues;
a is an integer from 3 to 10, preferably from 3 to 6 and
b is in each case independently of each other an integer from 1 to 3, preferably 1 or 2;
SP is independently of each other a compound group or is absent,
PG is a radically polymerizable group, and
n is an integer from 1 to 8, preferably 1 to 4, particularly preferably 1, 2 or 4,
wherein SP-PG and/or PG is bonded to MC via at least one of the Z residues and for X═NR$^1$ additionally or exclusively via at least one N atom (in this case at least one R$^1$═PG or SP-PG).

The variable b in formula IIb can represent the same integer in all cases or stand for two or three different numbers. Preferably, b has the same value each time it occurs in formula (IIb). If the radically polymerizable macrocyclic polyether or macrocyclic heteroanalogous polyether is a crown ether or heteroanalogous crown ether, i.e. MC conforms to formula IIa, then particularly preferably a=3, 4 or 5. If the radically polymerizable macrocyclic polyether is a cryptand according to formula IIb, then in a particularly preferred embodiment b=2.

The Z residues are selected independently of each other in each case from C$_1$-C$_4$ alkylene, C$_6$-C$_{10}$ arylene and C$_4$-C$_8$ cycloalkylene residues, preferably from ethylene, phenylene (particularly preferably 1,2-phenylene═o-phenylene) and cyclohexylene residues (particularly preferably 1,2-cyclohexylene). The above-named residues can in each case be substituted by an organic group, wherein a substitution with the PG and/or SP-PG residue is preferred. Examples of other suitable substituents include OH and COOH.

If the crown ether or heteroanalogous crown ether contains only O atoms or a combination of O and S atoms, then the n PG and/or SP-PG residues must be attached to the macrocycle MC via n Z residues. Preferred in this case are crown ethers or heteroanalogous crown ethers with a=4 or 5; in particular crown ethers with a=4; crown ethers with a=5; S-analogous crown ethers with a=5, in which two O atoms are replaced by S atoms. The n Z residues are then selected independently of each other from C$_1$-C$_4$ alkylene, C$_6$-C$_{10}$ arylene and C$_4$-C$_8$ cycloalkylene residues, preferably C$_6$-C$_{10}$ arylene and C$_4$-C$_8$ cycloalkylene residues and particularly preferably from phenylene and cyclohexylene residues. The remaining (a+1−n) Z residues are preferably ethylene.

If it is an N-analogous crown ether in which the O atoms are partially or completely replaced by NR$^1$ groups, e.g. N-analogous crown ethers with a=5 in which the X groups are a combination of O atoms and NR$^1$ groups, such as for example those in which two O atoms are replaced by NR$^1$ groups; or N-analogous crown ethers with a=3 in which all the O atoms are replaced by NR$^1$ groups, then the PG and/or SP-PG residues can be attached to the macrocycle MC additionally or exclusively via the N atoms of the NR$^1$ group(s). In this case, it is true for the corresponding NR$^1$ groups that R$^1$═PG and/or SP-PG. Preferably, the n PG and/or SP-PG residues are attached exclusively via the N atoms, i.e. in n NR$^1$ groups R$^1$═PG and/or SP-PG. The Z residues are then typically ethylene. However, it is also possible in the case of N-analogous crown ethers that all or some PG and/or SP-PG residues are attached via the Z residues. Where the n PG and/or SP-PG residues are attached exclusively via the Z residues, embodiments in which (a+1−n) Z residues are ethylene residues and n Z residues are PG- and/or SP-PG-substituted ethylene residues are preferred. A mixed attachment via N atoms and Z residues is also possible.

If the radically polymerizable macrocyclic heteroanalogous polyether is a cryptand, i.e. MC conforms to the formula IIb, then all the X groups are preferably O atoms.

In the case of the cryptands, the n PG and/or SP-PG residues are preferably attached to the macrocycle MC via n Z residues. These n Z residues are then selected independently of each other from PG- and/or SP-PG-substituted $C_1$-$C_4$ alkylene, $C_6$-$C_{10}$ arylene and $C_4$-$C_8$ cycloalkylene residues, preferably the n Z residues are PG- and/or SP-PG-substituted phenylene and/or ethylene. The remaining (2b+2−n) residues are preferably ethylene.

In the case of crown ethers or heteroanalogous crown ethers which contain only O atoms or a combination of O atoms with S atoms or $NR^1$ groups, preferably n=1 or 2. In the case of N-analogous crown ethers in which all the O atoms have been replaced by $NR^1$ groups, preferably n=1 or, in particular for a=3, n=4. In the case of cryptands preferably n=1.

In the case of N-analogous crown ethers which contain $NR^1$ groups in which $R^1 \neq PG$ or SP-PG, $R^1$ is hydrogen or any organic residue, e.g. —$(CH_2)_x$—CO—O—$R^2$ with x=1 to 5, preferably x=1, and $R^2$=H or $C_1$ to $C_6$ alkyl, preferably $R^2$=H, ethyl or t-butyl.

The polymerizable groups PG which are bonded to the macrocycle MC can be any radically polymerizable groups, i.e. groups which contain an ethylenically unsaturated double bond. Within an MC-(SP-PG)$_n$ molecule, for n>1 the n PG residues can be the same or different. Preferred polymerizable groups are vinyl, allyl and (meth)acryloyl groups, wherein the (meth)acryloyl groups can be for example part of a (meth)acryloyloxy or (meth)acryloylamino group. These groups, in particular the vinyl and allyl groups, can be substituted by further organic residues, e.g. with $C_1$ to $C_3$ alkyl, preferably methyl, or —CO—O—$R^3$, where $R^3$=H or $C_1$ to $C_3$ alkyl, preferably $R^3$=H or ethyl.

The above-named polymerizable groups PG can be bonded to the macrocycle MC directly or via a linking group ("spacer") SP, via the Z residues or N atoms as described above. Within an MC-(SP-PG)$_n$ molecule, for n>1 the linking groups can be the same or different or they can be wholly or partially omitted, i.e. within a molecule it is possible that the polymerizable groups PG are bonded to MC in part directly and in part via the spacer SP.

The linking groups SP preferably conform to the formula —$R^4$—$Z^1$—$R^5$—$Z^2$—, where $Z^1$ and $Z^2$ are the same or different and in each case stand for —O—, —NH—, —CO—O—, —O—CO—, —CO—NH—, —NH—CO—, —O—CO—NH— or —NH—CO—O— or one or both of $Z^1$ and $Z^2$ are omitted and $R^4$ and $R^5$ are the same or different and in each case stand for a $C_1$-$C_{10}$ alkylene residue or one or both of $R^4$ and $R^5$ are omitted. It has been shown that MC-(SP-PG)$_n$ molecules in which the polymerizable group PG is bonded to MC via a linking group SP, often have a greater polymerizability than molecules in which the polymerizable group PG is bonded directly to MC.

Examples of PG residues which can be bonded to Z residues directly or via SP include: vinyl (preferably bonded to Z=phenylene); allyl ether (preferably bonded to Z=phenylene or ethylene); (meth)acryloyloxyalkyl, preferably (meth)acry-loyloxymethyl (preferably bonded to Z=phenylene, cyclohexylene or ethylene), and (meth)acryloylaminoalkyl, preferably (meth)acryloylaminomethyl and -propyl (preferably bonded to Z=phenylene or ethylene). Examples of PG residues which can be bonded to N atoms directly or via SP include: (meth)acryloyl which forms a (meth)acrylamide with the N atom of the macrocycle; carboxyallyl; alkoxycarbonyl allyl, preferably ethoxycarbonyl allyl and t-butoxycarbonyl allyl, and (meth)acryloylaminoalkanoyl, preferably (meth)acryloylaminohexanoyl.

The radically polymerizable macrocyclic polyethers and macrocyclic heteroanalogous polyethers of the present invention can be prepared by known synthesis processes (see for instance C. J. Pedersen, H. K. Frensdorf, Angew. Chem. 84 (1972) 16 et seq.; Studies in Organic Chemistry, Vol. 45: Crown Ethers and Analogous Compounds, Ed. M. Hiraoka, Elsevier, Amsterdam etc 1992, 17 et seq.). Thus e.g. polymerizable crown ethers with an aromatic ring (X=O; a=3 to 10; a Z residue is an o-phenylene group substituted in 4-position and the remaining Z residues are ethylene) can be prepared by multi-stage synthesis in such a way that the dichloride Cl—$(CH_2CH_2O)_xCH_2CH_2$—Cl (with x=2 to 8) is first condensed with p-4-chloromethylcatechol. The substituted benzo-crown ether obtained is then converted to the corresponding methacrylate with the sodium salt of the methacrylic acid:

1$^{st}$ stage:

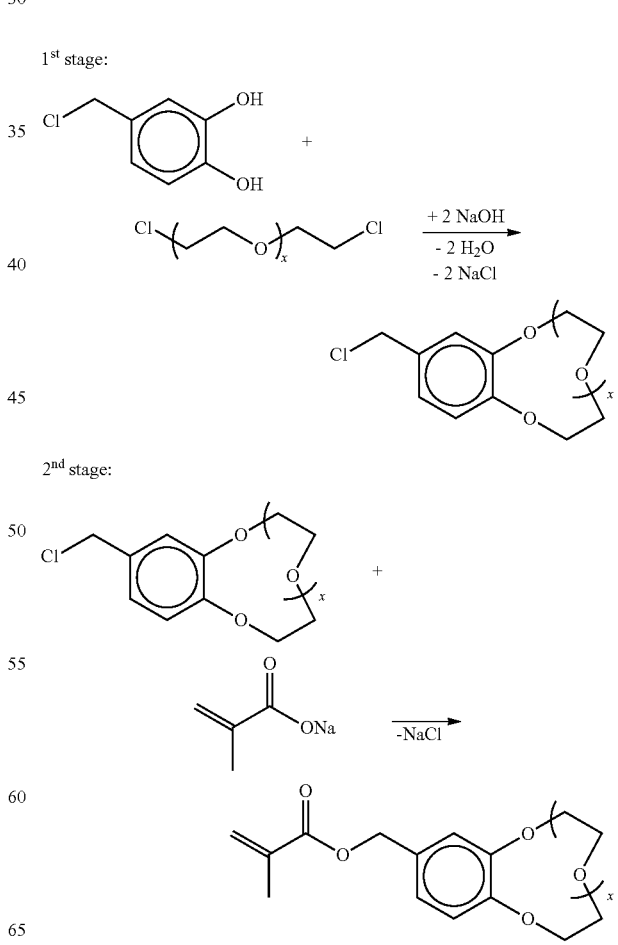

2$^{nd}$ stage:

Specific Example

Synthesis of
4-methacryloyloxymethylbenzo-18-crown-6

1st stage:

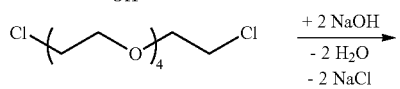

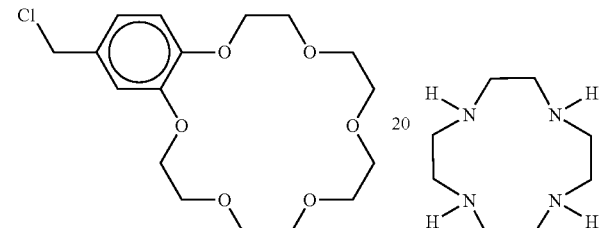

2nd stage:

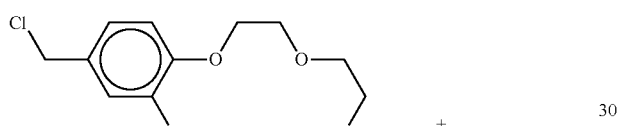

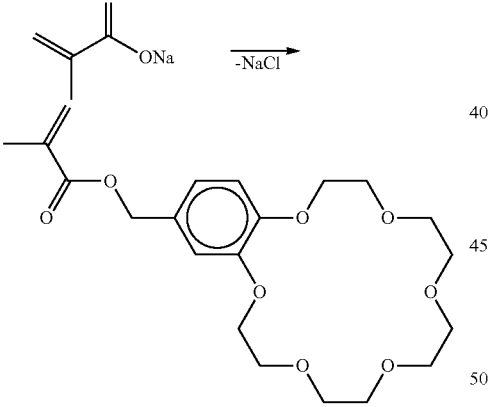

If suitable functionalized crown ethers are already present, they can be converted into polymerizable derivatives using methods known from organic chemistry. Thus for example N-analogous crown ethers, such as e.g. tetra-aza macrocycles, can easily be functionalized by acylation or alkylation:

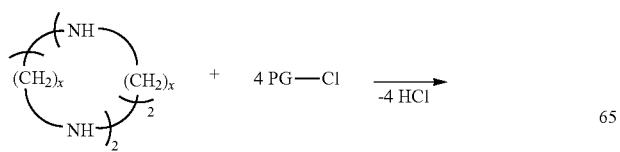

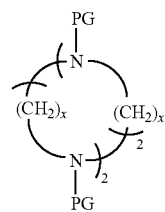

($x$ = 1 to 4, preferably 2)

Specific Example

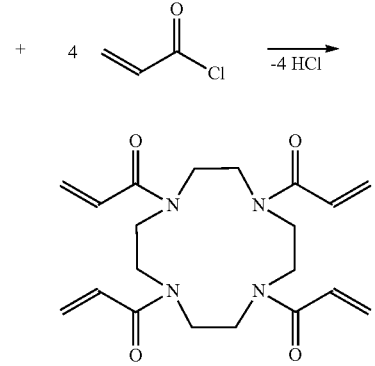

Examples of radically polymerizable macrocyclic polyethers and macrocyclic heteroanalogous polyethers for use in the present invention are:

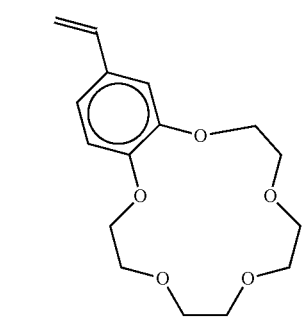

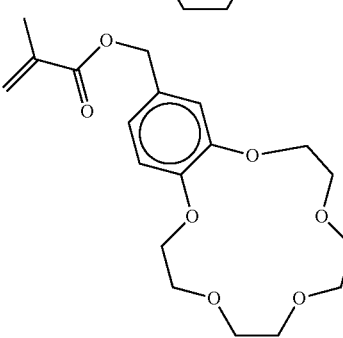

-continued
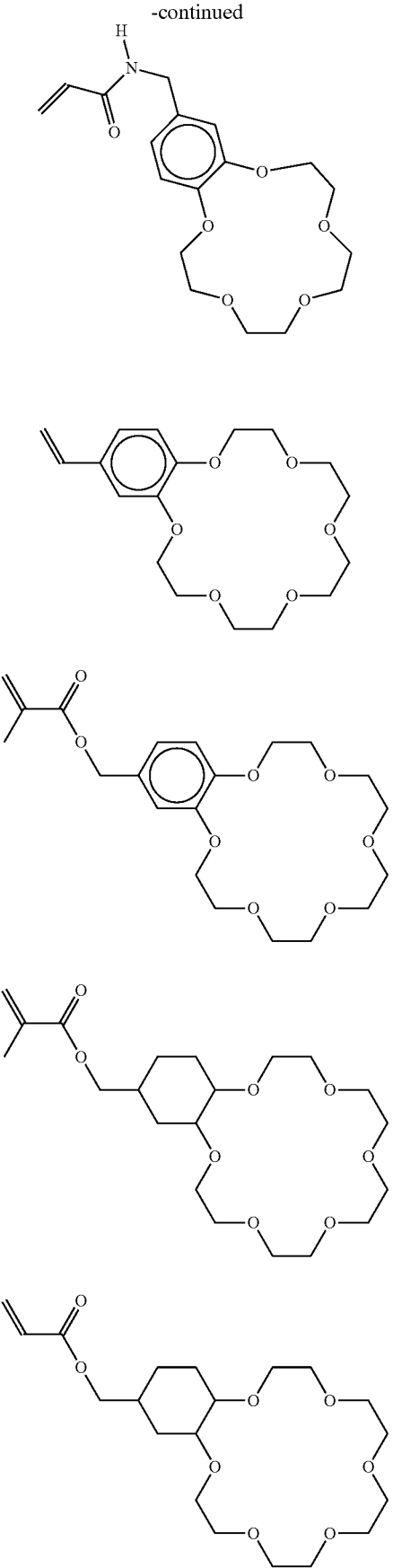
-continued
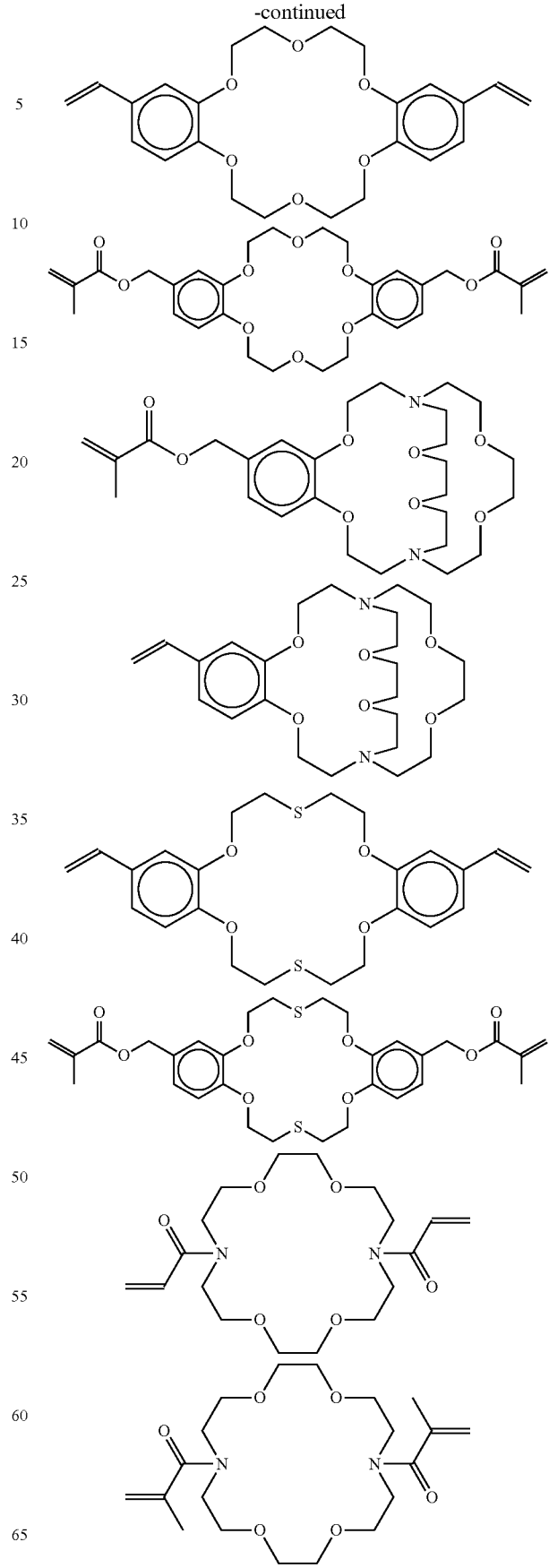

-continued
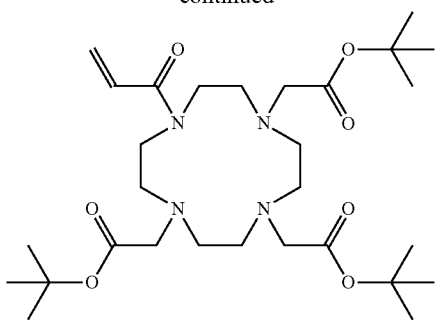
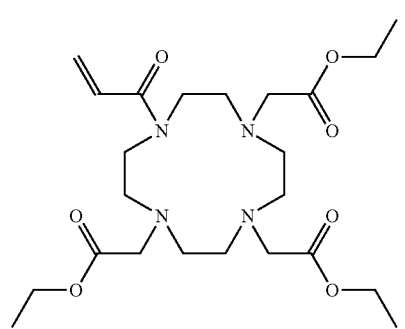
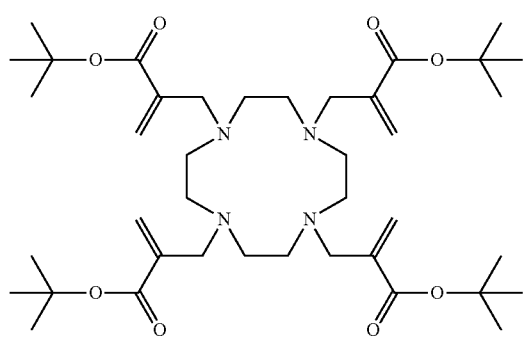
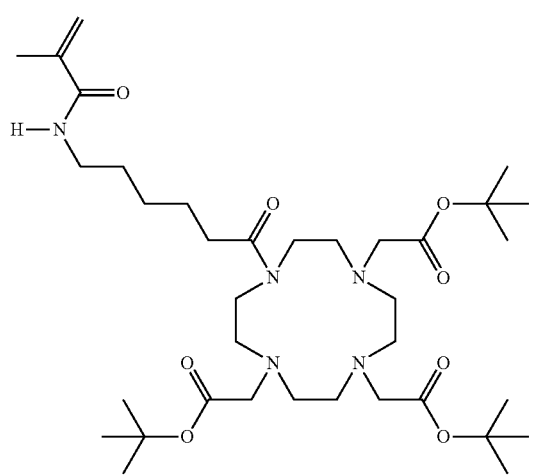
-continued
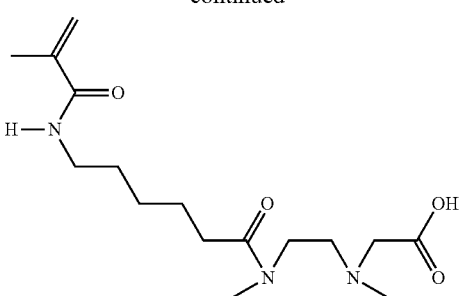
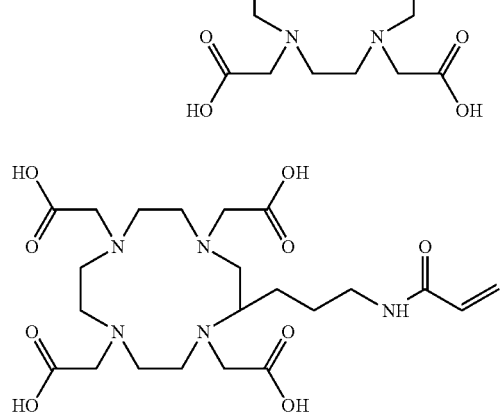
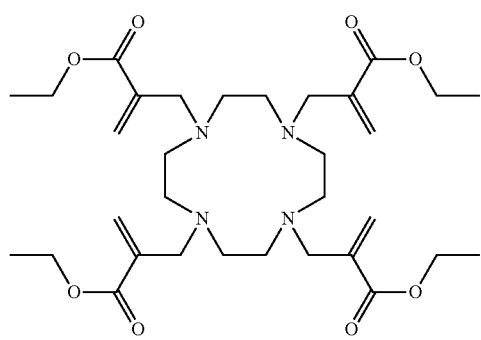
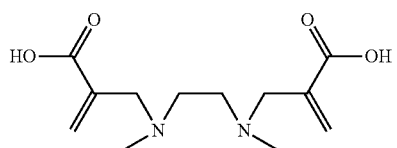
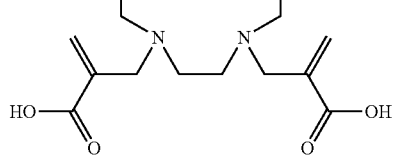
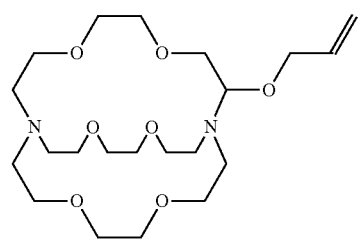

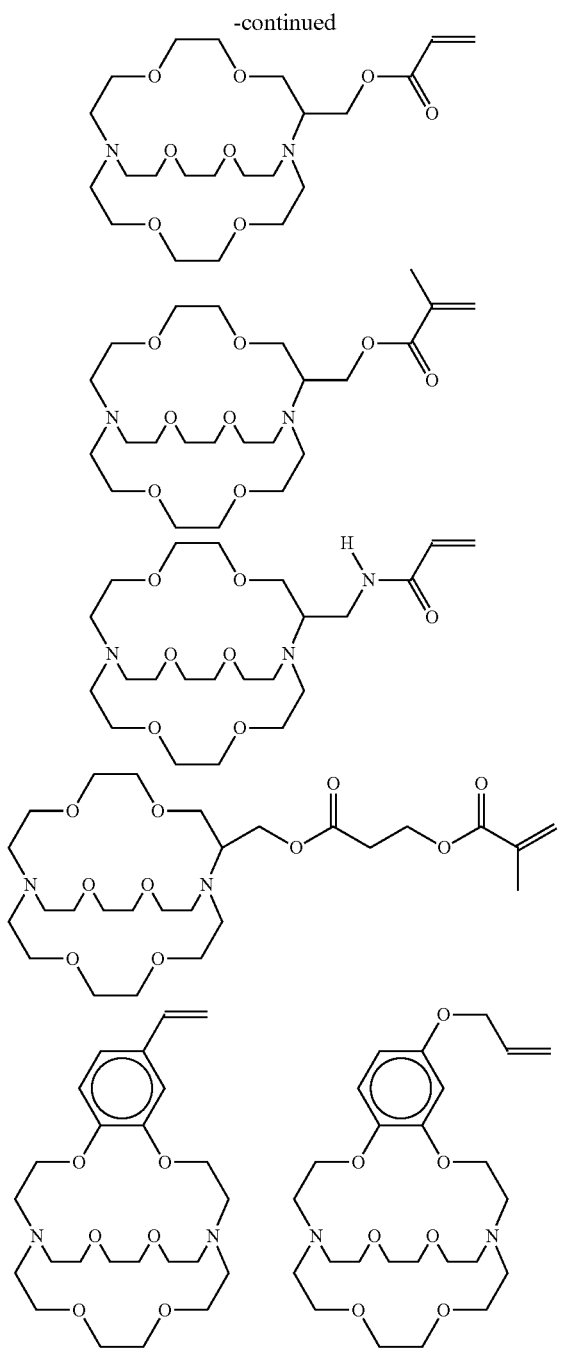

The radically polymerizable macrocyclic polyethers and/or macrocyclic heteroanalogous polyethers are typically contained in the dental materials according to the invention in a quantity of 0.05 to 40 wt.-%, preferably 1 to 30 wt.-% and particularly preferably 1 to 20 wt.-%, in each case relative to the total weight of the dental material. Only one type of radically polymerizable macrocyclic polyether or macrocyclic heteroanalogous polyether, or mixtures of different radically polymerizable macrocyclic polyethers and/or macrocyclic heteroanalogous polyethers, can be included.

The dental materials according to the present invention are typically adhesives, coating materials, cements or composites for dental purposes.

The radically polymerizable macrocyclic polyethers or macrocyclic heteroanalogous polyethers in the dental materials according to the invention are very soluble in water or mixtures of water with polar solvents, such as acetone, ethanol or acetonitrile. As phase transfer catalysts, they promote the wetting of organic components on the most varied substrate surfaces or the diffusion of compounds into the inside of porous materials. In addition, the radically polymerizable macrocyclic polyethers and macrocyclic heteroanalogous polyethers can complex metal ions, such as e.g. calcium ions, and are therefore in a position to mediate the adhesion on tooth enamel and dentine. In the monomers used according to the invention, the macrocycles are covalently connected to the polymerizable groups directly or via linking groups, with the result that the macrocyclic components are covalently integrated into the polymerizate after polymerization, which improves the biocompatibility of the corresponding materials.

The dental materials according to the invention can furthermore contain additional radically polymerizable matrix monomers which differ from the radically polymerizable macrocyclic polyether or macrocyclic heteroanalogous polyether. It is understood that mixtures of different additional monomers or only one type of an additional monomer can be present.

Examples of suitable additional radically polymerizable monomers are mono- or polyfunctional (meth)acrylates, such as for instance methyl, ethyl, hydroxyethyl, butyl, benzyl, tetrahydrofurfuryl and isobornyl (meth)acrylate, bisphenol A di(meth)acrylate, Bis-GMA (an addition product of methacrylic acid and bisphenol A diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, and also glycerol dimethacrylate, 1,4-butanediol di(meth)acrylate, 1,10-decanediol di(meth)acrylate and 1,12-dodecanediol di(meth)acrylate.

Further suitable additional radically polymerizable monomers are hydrolysis-resistant diluting monomers, such as for instance hydrolysis-resistant mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- and disubstituted acrylamides, such as e.g. N-ethyl acrylamide, N,N-dimethacrylamide, N-(2-hydroxyethyl)acrylamide and N-methyl-N-(2-hydroxyethyl)acrylamide, or N-monosubstituted methacrylamides, such as e.g. N-ethylmethacrylamide and N-(2-hydroxyethyl)methacrylamide and in addition N-vinylpyrrolidone and allyl ether.

Examples of hydrolysis-resistant cross-linking monomers which can also be used in the dental materials according to the invention are urethanes of 2-(hydroxymethyl)acrylic acid esters and diisocyanates, such as 2,2,4-trimethylhexamethylene diisocyanate or isophorone diisocyanate, cross-linking pyrrolidones, such as e.g. 1,6-bis(3-vinyl-2-pyrrolidonyl)-hexane, and commercially available bisacrylamides such as methylene- and ethylenebisacrylamides, or bis(meth)acrylamides, such as e.g. N,N'-diethyl-1,3-bis(acrylamido)propane, 1,3-bis(methacrylamido)propane, 1,4-bis(acrylamido)butane and 1,4-bis(acryloyl)piperazine which can be synthesized with (meth)acrylic acid chloride by reaction from the corresponding diamines.

As additional radically polymerizable monomers, furthermore, known low-shrinkage monomers which are polymerizable radically in a ring-opening manner, such as e.g. mono- or multifunctional vinylcyclopropanes or bicyclic cyclopropane derivatives (see DE-C-196 16 183 or EP 1 413 569 A) or cyclic allyl sulphides (see U.S. Pat. No. 6,043,361 or U.S. Pat. No. 6,344,556) can also be used, which can in addition also be used in combination with the above-listed di(meth)acrylate cross-linkers. Suitable monomers polymerizable in a ring-opening manner are in particular vinylcyclopropanes, such as 1,1-di(ethoxycarbonyl) and 1,1-di(methoxycarbonyl)-2-vinylcyclopropane, and the esters of 1-ethoxycarbonyl and 1-methoxycarbonyl-2-vinylcyclopropane carboxylic acid with ethylene glycol, 1,1,1-trimethylolpropane, 1,4-cyclohexanediol or resorcinol. Suitable bicyclic cyclopropane derivatives are 2-(bicyclo[3.1.0]hex-1-yl)acrylic acid methyl and ethyl esters and their disubstitution products in 3-position, such as (3,3-bis(ethoxycarbonyl)bicyclo[3.1.0]hex-1-yl)acrylic acid methyl or ethyl esters. Suitable cyclic allyl sulphides are the addition products of 2-(hydroxymethyl)-6-methylene-1,4-dithiepane or 7-hydroxy-3-methylene-1,5-dithiacyclooctane with 2,2,4-trimethyl-hexamethylene-1,6-diisocyanate or the asymmetric hexamethylene diisocyanate trimer (the asymmetric trimer has an iminooxadiazine dione structure unlike the symmetric hexamethylene diisocyanate trimer with an isocyanurate structure). Asymmetric hexamethylene diisocyanate trimers are commercially available for example from Bayer AG under the name Desmodur® VP LS 2294.

As additional monomers, radically polymerizable polysiloxanes can also be used which can be prepared from suitable methacrylic silanes, such as e.g. 3-(methacryloyloxy)propyltrimethoxysilane, and are described e.g. in DE-C-199 03 177.

Finally, mixtures of the above-named monomers with radically polymerizable, acid group-containing adhesive monomers can also be used as additional radical polymerizable matrix monomers. Suitable acid group-containing monomers are polymerizable carboxylic acids, such as maleic acid, acrylic acid, methacrylic acid, 2-(hydroxymethyl)acrylic acid, 4-(meth)acryloyloxyethyl trimellitic acid anhydride, 10-methacryloyloxydecylmalonic acid, N-(2-hydroxy-3-methacryloyloxypropyl)-N-phenylglycine or 4-vinylbenzoic acid. Examples of suitable phosphonic acid monomers are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid and 2-[2-dihydroxyphosphoryl)-ethoxymethyl]-acrylic acid ethyl and -2,4,6-trimethylphenyl esters. Examples of suitable acidic polymerizable phosphoric acid esters are 2-methacryloyloxypropyl mono- and dihydrogen phosphate, 2-methacryloyloxyethyl mono- and dihydrogen phosphate, 2-methacryloyloxyethyl phenyl hydrogen phosphate, dipentaerythritol pentamethacryloyloxy phosphate, 10-methacryloyloxydecyl dihydrogen phosphate, dipentaerythritol-pentamethacryloyloxy phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl dihydrogen phosphate. Examples of suitable polymerizable sulphonic acids are vinyl sulphonic acid, 4-vinylphenyl sulphonic acid and 3-(methacrylamido)propyl sulphonic acid.

The dental materials according to the invention typically contain an initiator for the radical polymerization. The initiator is selected in dependence on what type of curing is desired for the dental material according to the invention, e.g. radiation curing (photopolymerization) and/or hot curing and/or curing at room temperature.

Benzophenone, benzoin, and their derivatives or α-diketones or their derivatives such as 9,10-phenanthrenequinone, 1-phenylpropane-1,2-dione, diacetyl or 4,4-dichlorobenzil for example are used to initiate the radical photopolymerization. Preferably, camphorquinone or 2,2-methoxy-2-phenyl acetophenone and particularly preferably α-diketones in combination with amines are used as reducing agents, such as e.g. 4-(dimethylamino)benzoic acid esters such as p-N,N-dimethylaminobenzoic acid ethyl ester, N,N-dimethylaminoethyl methacrylate, N,N-dimethyl-sym.-xylidine or triethanolamine. Norrish type I photoinitiators are also particularly suitable, above all acyl- or bisacylphosphine oxides, monoacyltrialkyl or diacyldialkyl germanium compounds, such as e.g. benzoyltrimethyl germanium, dibenzoyl diethyl germanium and bis(4-methoxybenzoyl)diethyl germanium. Mixtures of the different photoinitiators can also be used, such as e.g. dibenzoyl diethyl germanium in combination with camphorquinone and 4-dimethylaminobenzoic acid ethyl ester.

Suitable as initiators for the hot curing are e.g. benzopinacol or 2,2'-dialkylbenzopinacols.

As initiators for a polymerization carried out at room temperature, redox initiator combinations are typically used, such as e.g. combinations of benzoyl peroxide with N,N-dimethyl-sym.-xylidine or N,N-dimethyl-p-toluidine. In addition, redox systems consisting of peroxides and reductants such as e.g. ascorbic acid, barbiturates or sulphinic acids are also particularly suitable.

The total initiator quantity is typically 0.01 to 10 wt.-%, preferably 0.1 to 3.0 wt.-% and particularly preferably 0.1 to 1.0 wt.-%, in each case relative to the total weight of the dental material.

Furthermore, the dental materials according to the invention can optionally be filled with organic or inorganic particles to improve the mechanical properties or to adjust the viscosity. The fillers preferably have a particle size of 5 nm to 2,000 µm, preferably 10 nm to 1,000 µm. Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or micro-fine fillers, such as pyrogenic silicic acid and precipitation silicic acid, as well as minifillers, such as quartz, glass ceramic and glass powder with an average particle size of 0.01 to 1 µm as well as x-ray opaque fillers, such as ytterbium trifluoride and nanoparticulate tantalum(V) oxide or barium sulphate. Mixtures of different fillers can also be used as filler. Within the meaning of this invention, by nanoparticulate fillers are meant fillers with a particle size of 5 to 10 nm, by micro-fine fillers are meant fillers with a particle size of 10 nm to 100 nm and by minifillers are meant fillers with a particle size of 10 to 1,000 nm.

Optionally—preferably, if the dental material is an adhesive or a coating material—the dental material according to the invention can contain solvent or a mixture of solvent. Water, ethanol and mixtures of water with acetone and/or ethanol are preferred.

Optionally, the dental material according to the invention can contain one or more further additives, e.g. stabilizers, aromatics, colourants, microbicidal agents, fluoride ion-releasing additives, optical brighteners, plasticizers and UV absorbers.

The radically polymerizable macrocyclic polyethers or macrocyclic heteroanalogous polyethers can for example be incorporated into the dental composition in pure form or, in the case of composites or cements, also as a solution in monomers, in the case of adhesives or coating materials, as a solution in a suitable solvent. The incorporation preferably takes place by means of usual dispersing methods, such as e.g. stirring or kneading.

In typical embodiments, the dental material according to the present invention contains:

(i) 0.05 to 40 wt.-%, preferably 1 to 30 wt.-% and particularly preferably 1 to 20 wt.-% of the radically polymerizable macrocyclic polyether and/or macrocyclic heteroanalogous polyether,
(ii) 0.01 to 10 wt.-%, particularly preferably 0.1 to 3.0 wt.-% of an initiator for the radical polymerization,
(iii) 0 to 80 wt.-%, preferably 0 to 60 wt.-% and particularly preferably 5 to 50 wt.-% of at least one radically polymerizable monomer which is different from component (i),
(iv) 0 to 75 wt.-%, depending on the application preferably 0 to 20 wt.-% (in the case of adhesives and coating materials) or 20 to 75 wt.-% (in the case of cements and composites) of filler,
(v) 0 to 95 wt.-%, preferably 0 to 70 wt.-% and particularly preferably 5 to 50 wt.-% of solvent in the case of adhesives or coating materials, in each case relative to the total weight of the dental material.

The invention is described in further detail below with reference to examples which are meant to be exemplary only, and non-limiting.

EXAMPLES

Example 1

Synthesis of 4-(methacryloyloxymethyl)benzo-15-crown-5 (MA15-C5)

The synthesis of the polymerizable crown ether MA15-05 took place in 2 stages analogously to the literature (A. J. Varma, T. Majewicz, J. Smid, J. Polym. Sci., Polym. Chem. Ed., 17 (1979) 1573):

1st Stage 4-hydroxymethylbenzo-15-crown-5

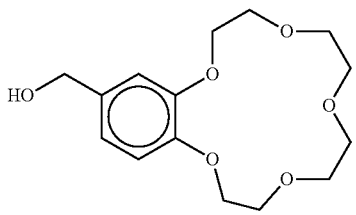

Sodium borohydride (2.49 g, 65 mmol) was added under stirring to a suspension of 4-formylbenzo-15-crown-5 (16.24 g, 54.8 mmol), which was prepared in accordance with A. J. Varma, J. Smid, J. Polym. Sci., A-1, 15 (1977) 1189, in 300 ml absolute ethanol, and the mixture left to react further for 24 h. It was quenched with 300 ml water and neutralized with 15 ml 25% acetic acid. The aqueous phase was extracted 4 times in each case with 125 ml chloroform and the combined organic phases dried over anhydrous $Na_2SO_4$ and filtered. The filtrate was concentrated on the rotary evaporator and dried under fine vacuum. 15.60 g of a yellowish oil was obtained, which was dissolved in 10 ml acetone and filtered over a fritted-glass filter filled with silica gel (silica gel 60, 0.035-0.070 mm, 60 g, Ø50 mm; THF, elution volume: 600 ml). After a renewed concentration and drying in the fine vacuum, 14.88 g (49.9 mmol, 91% yield) of a colourless oil was obtained (solidified slowly to a white solid, HPLC purity: 95.7%).

$^1$H-NMR ($CDCl_3$, 400 MHz): δ=2.75 (b, 1H, OH), 3.75 (s, 8H, $CH_2O(C_2\underline{H}_4O)_2CH_2$), 3.87 (q, 4H, $ArOCH_2C\underline{H}_2$), 4.09 (q, 4H, $ArOC\underline{H}_2CH_2$), 4.55 (s, 2H, $CH_2Ar$), 6.79-6.86 (m, 3H, $^{2,5,6}$H—Ar).

IR (KBr): 3431, 2930, 2875, 1592, 1515, 1451, 1426, 1370, 1356, 1325, 1287, 1259, 1236, 1161, 1128, 1088, 1045, 960, 935, 880, 844, 825, 804, 784, 745 cm$^{-1}$.

2nd Stage 4-(methacryloyloxymethyl)benzo-15-crown-5 (MA15-C5)

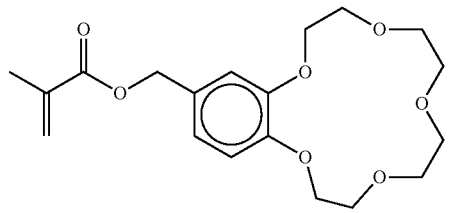

A solution of 4-(hydroxymethyl)benzo-15-crown-5 (7.68 g, 25.7 mmol), triethylamine (2.61 g (25.7 mmol) and 4-dimethylaminopyridine, 122 mg, 1.0 mmol) in 150 ml dichloromethane was cooled to −5° C. and a solution of methacrylic acid anhydride (3.97 g, 25.7 mmol) and BHT (butylated hydroxytoluene) (10 mg) in 30 ml dichloromethane was then added dropwise over 10 min under stirring. The clear, colourless solution was stirred for a further 1 h at −5° C. and for 18 h at room temperature and then washed 3 times with 100 ml water each time. The combined aqueous phases were extracted twice with 50 ml dichloromethane each time and the combined organic phases dried over anhydrous $Na_2SO_4$. It was filtered, concentrated on the rotary evaporator after the addition of 5 mg BHT and dried under fine vacuum.

8.95 g of a light reddish solid was obtained which was dissolved in 10 ml dichloromethane and purified by means of MPLC (silica gel 60, 0.015-0.040 mm, 85 g, Ø40 mm×15 cm; eluent: n-hexane/ethyl acetate 1:1). 5.68 g (15.5 mmol; 60% yield) of a white solid (HPLC purity: 97.4%) was obtained. Melting point: 75.2° C.-76.6° C.

$^1$H-NMR ($CDCl_3$, 400 MHz): δ=1.95 (s, 3H, $CH_3$), 3.77 (s, 8H, $C_2H_4OC_2\underline{H}_4OC_2H_4$), 3.91 (q, 4H, $C\underline{H}_2CH_2OAr$), 4.14 (q, 4H, $CH_2OAr$), 5.10 (s, 2H, $CH_2OC=O$), 5.57 and 6.12 (s, 2×1H, =$CH_2$), 6.83-6.94 (m, 3H, $^{2,5,6}$H—Ar).

IR (KBr): 2927, 2871, 1712, 1635, 1592, 1524, 1457, 1431, 1343, 1316, 1268, 1246, 1165, 1133, 1116, 1081, 1054, 1007, 979, 953, 932, 896, 876, 815, 798, 786, 742, 639 cm$^{-1}$.

Example 2

Synthesis of 2-[4,7,10-tris-(2-tert-butoxycarbonylallyl)-1,4,7,10-tetraazacyclododec-1-ylmethyl]acrylic acid-tert-butyl ester (V-621)

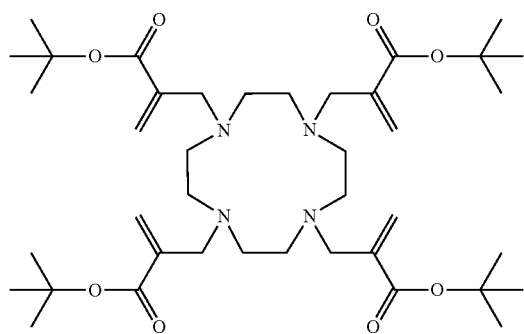 [SMILES: C=C(CN1CCN(CC(=C)C(=O)OC(C)(C)C)CCN(CC(=C)C(=O)OC(C)(C)C)CCN(CC(=C)C(=O)OC(C)(C)C)CC1)C(=O)OC(C)(C)C]

Cyclen (1,4,7,10-tetraazacyclododecane) (8.6 g, 0.05 mol) was dissolved in 250 ml anhydrous acetonitrile, potassium carbonate (27.6 g, 0.2 mol) was added and a solution of 2-bromomethylacrylic acid tert-butyl ester (44.2 g, 0.2 mol) and 20 mg BHT in 125 ml anhydrous acetonitrile was then added dropwise under stirring and ice-bath cooling. The mixture was left over night at room temperature to react further and the precipitated deposit was then removed by suction, suspended in 250 ml deionized water and stirred vigorously for 1 h. Renewed removal by suction was carried out, followed by washing with water and drying in the vacuum drying oven at 50° C. 29.0 g (79% yield) of a white solid was obtained (m.p.: 121-122° C.). (CDCl$_3$, 400 MHz): δ=1.49 (s, 36H, CH$_3$), 2.58 (s, 16H, CH$_2$CH$_2$), 3.10 (s, 8H, CH$_2$C=), 5.97 and 6.12 (s, 2×4H, CH$_2$=).

IR (KBr): 2976, 2950, 2810, 1701, 1636, 1477, 1453, 1434, 1389, 1368, 1354, 1318, 1295, 1257, 1129, 1078, 1017, 992, 975, 954, 940, 922, 852, 823, 761, 679, 648 cm$^{-1}$.

Example 3

Synthesis of 1-acryloyl-4,7,10-tris(tert-butoxycarbonylmethyl)-1,4,7,10-tetraazacyclododecane (MA-439)

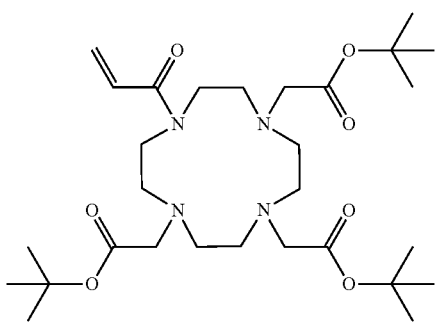 [SMILES: C=CC(=O)N1CCN(CC(=O)OC(C)(C)C)CCN(CC(=O)OC(C)(C)C)CCN(CC(=O)OC(C)(C)C)CC1]

A solution of freshly distilled acrylic acid chloride (1.41 g, 15.6 mm) in 10 mg BHT and 200 ml dichloromethane (dried over a 4 Å molecular sieve) was added dropwise at −5 to 0° C. over 90 min to a suspension of 1,4,7-tris(tert-butoxycarbonylmethyl)-1,4,7,10-tetraazacyclododecane hydrobromide (8.45 g, (14.2 mmol), sodium hydroxide (1.25 g 31.2 mmol) and 60 ml deionized water. After the addition was completed, the reaction mixture was stirred for 1 h at 0° C., then removed from the ice bath and stirred for a further 3 h at room temperature. The aqueous phase was saturated by adding 10 g NaCl and extracted twice with in each case 40 ml dichloromethane. The combined organic phases were dried over anhydrous Na$_2$SO$_4$, filtered and concentrated on the rotary evaporator after the addition of 5 mg BHT and further dried in fine vacuum. 8.23 g of a high-viscosity crude product was obtained which was purified by column chromatography (silica gel 60, 0.035-0.070 mm) first with acetone and then with n-hexane/ethyl acetate 1:1 as eluent. After the concentration accompanied by addition of BHT and drying at 50° C., 4.77 g (8.4 mmol, 59% yield) of a highly viscous, colourless oil was obtained (HPLC purity: 96%).

$^1$H-NMR (CDCl$_3$, 400 MHz): δ=1.44, 1.45 and 1.46 (s, 3×9H, CH$_3$), 2.70-2.77 (m, 8H, O=CCH$_2$NC$_2$H$_4$NCH$_2$C=O), 2.96 and 3.02 (m 2×2H, CH$_2$CH$_2$NC=O), 3.27, 3.30 and 3.32 (s, 3×2H, all CH$_2$C=O), 3.61 and 3.75 (t, 2×2H, CH$_2$NC=O), 5.60-5.65, 6.28-6.35 and 6.56-6.65 (m, 3×1H, CH=CH$_2$).

IR (neat): 2976, 2931, 2824, 1722, 1647, 1610, 1440, 1392, 1366, 1290, 1248, 1216, 1146, 1051, 979, 950, 914, 847, 795, 744.

Example 4

Synthesis of {4,7-bis-tert-butoxycarbonylmethyl-10-[6-(2-methyl-acryloylamino)hexanoyl]-1,4,7,10-tetraazacyclododec-1-yl}acetic acid-tert.-butyl ester (MA-442)

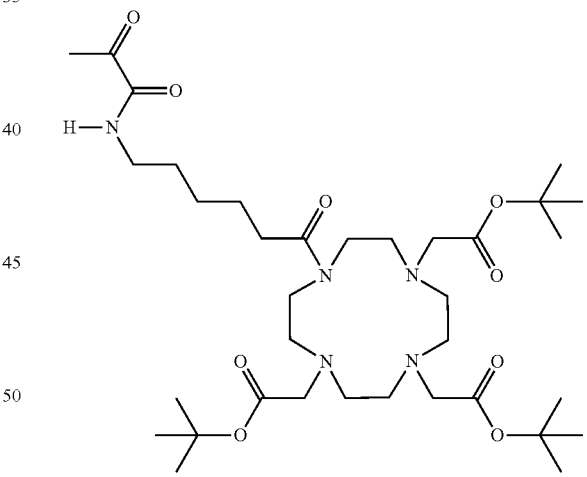

A suspension of 6-(methacryloylamino)caproic acid (2.80 g, 14.0 mmol), 1,4,7-tris(tert-butoxycarbonylmethyl)-1,4,7,10-tetraazacyclododecane hydrobromide (7.75 g, 13.0 mmol), N,N-dimethylaminopyridine (1.83 g, 15.0 mmol) and 5 mg BHT in 60 ml dichloromethane was cooled to −5° C. and 1-ethyl-3-(3-dimethylaminopropyl)carbodiimide hydrochloride (2.88 g, 15.0 mmol) was added portionwise under stirring. To complete the reaction, the mixture was stirred for 2 h at −5° C. and over night at room temperature. 1-ethyl-3-(3-dimethylaminopropyl)carbodiimide hydrochloride (1.00 g, 6.44 mmol) and N,N-dimethylaminopyridine (0.6 g, 4.9 mmol) each time were then added 3 more times at intervals of 2 h and finally left to be stirred for 6 h. The solution was washed 3 times with in each case 50 ml saturated aqueous NaCl solution, dried over anhydrous Na$_2$SO$_4$, filtered, concentrated on the rotary evaporator after the addition of 5 mg BHT and dried under fine vacuum. 10.3 g of a yellowish oil was obtained which was purified twice by chromatography (silica gel 60, 0.015-0.040 mm, acetone). The acetone was again distilled off on the rotary evaporator after the addition of 5 mg BHT and the product dried in fine vacuum. 6.13 g (8.8 mmol, 68% yield) of a yellow, highly viscous oil was obtained (HPLC purity: 95%).

$^1$H-NMR (CDCl$_3$, 400 MHz): δ=1.31-1.72 (m, 6H, (CH$_2$)$_3$CH$_2$N, 1.46 (s, 27H, t-Bu), 1.96 (s, 3H, CH$_3$C=), 2.32 (t, 2H, CH$_2$CH$_2$C=O) 2.73, (b, 6H, CH$_2$N), 2.81, 2.89 and 2.98 (b, 3×2H, CH$_2$N), 3.27 and 3.32 (b, 2×4H, CH$_2$N), 3.54 and 3.66 (b, 2×2H, CH$_2$N), 5.30 and 5.69 (s, 2×1H, CH$_2$=); 6.19 (b, 1H, NH).

IR: 3320, 2970, 2931, 2860, 1724, 1619, 1530, 1455, 1392, 1366, 1305, 1216, 1147, 934, 920, 846, 744 cm$^{-1}$.

Example 5

Radical Homopolymerization of MA15-C5 in Solution

The monomer MA15-C5 (0.05 mol/l) was polymerized in toluene with 2,2'-azobisisobutyronitrile (AIBN, 2.0 mol-%) at 65° C. After 15 h, the polymerization was stopped and the polymerizate precipitated out of 10 times the quantity of n-hexane, filtered off and dried in fine vacuum until the weight was constant. A white polymer was obtained in 93% yield. The polymer structure was verified by means of $^1$H and $^{13}$C-NMR spectroscopy:

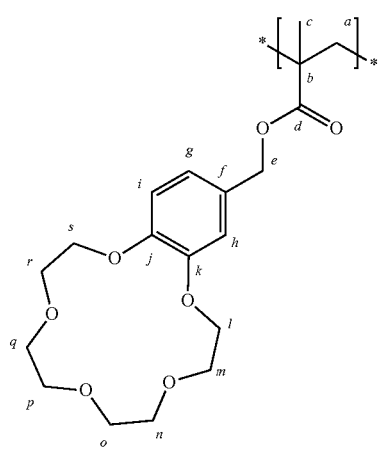

$^1$H-NMR (400 MHz, CDCl$_3$, δ ppm): 0.73-1.16 (H$_c$, m, 3H), 1.78-2.50 (H$_a$, m, 2H), 3.71 (H$_n$, H$_o$, H$_p$, H$_q$, s, 8H), 3.84 (H$_m$, H$_r$, s, 4H), 4.07 (H$_l$, H$_s$, s, 4H), 4.80 (H$_e$, s, 2H), 6.80 (H$_g$, H$_h$, H$_i$, m, 3H).

$^{13}$C-NMR (100 MHz, CDCl$_3$, δ ppm): 16.7+18.9 C$_c$, 45.0 C$_b$, 66.8 C$_e$, 66.9-71.1 C$_l$-C$_s$, 113.7 C$_h$, 114.6 C$_i$, 121.8 C$_g$, 128.3 C$_f$, 149.0 C$_j$+C$_k$, 177.1 C$_d$.

Example 6

Cross-Linking Radical Polymerization to Determine the Reactivity in the Radical Polymerization Homogeneous mixtures of monomers and solvents, each given in Table 1, and also 1% AIBN were prepared in Schlenk vessels and degassed over a period of 20 min by passing argon through them. The polymerization batches were then heated to 65° C. in a thermostat. The time in which a three-dimensional, firm gel formed was determined as the gelling time.

TABLE 1

Composition of the monomer mixtures (values in wt.-%)

| Monomer | Solvent | Gelling time (min) |
|---|---|---|
| 15% MA-439 and 15% GDMA | 69% DMF | 15 |
| 15% MA-442 and 15% GDMA | 69% toluene | 5 |

The Example 6 proves that the radical polymerization capability of MA-442, in which the polymerizable group is attached to the N-heteroanalogous crown ether ring via a spacer, is clearly greater than that of MA-439, in which the methacryloyl group is covalently bonded directly to the ring.

Example 7

Preparation of a Dentine Adhesive Based on MA15-C5

In order to study dentine adhesion on bovine tooth dentine, an adhesive with the composition given in Table 2 was prepared:

TABLE 2

Composition of the adhesive (values in wt.-%)

| Component | Percentage by weight |
|---|---|
| MA15-C5 | 5.9 |
| EAEPA[1] | 5.0 |
| Glycerol dimethacrylate | 9.9 |
| UDMA[2] | 9.9 |
| Bis-GMA[3] | 32.7 |
| 2-hydroxyethyl methacrylate | 14.9 |
| Photoinitiator[4] | 1.7 |
| Ethanol (abs.) | 20.0 |

[1]EAEPA (2[4-(dihydroxyphosphoryl)-2-oxa-butyl]-acrylic acid ethyl ester),
[2]UDMA (addition product of 2-hydroxyethyl methacrylate and 2,2,4-trimethylhexamethylene diisocyanate),
[3]Bis-GMA (addition product of methacrylic acid and bisphenol A diglycidyl ether),
[4]Mixture of camphorquinone (0.2%), 4-dimethylbenzoic acid ethyl ester (0.5%) and the acylphosphine oxide Lucirin TPO (1.0%)

Bovine teeth were embedded in plastic cylinders in such a way that the dentine and the plastic were on one level. After 15 s etching with 37% phosphoric acid, they were rinsed thoroughly with water. A layer of adhesive with the above composition was then brushed on with a microbrush, briefly blown with an air blower to remove the solvent and exposed to light for 40 s with a halogen light (Astralis® 7, Ivoclar Vivadent AG). A composite cylinder of Tetric® Ceram (Ivoclar Vivadent AG) is polymerized onto the adhesive layer in two layers of 1-2 mm each. The testpieces were then stored in water for 24 h at 37° C. and the adhesive shear strength measured according to the ISO guideline "ISO 2003-ISO TR 11405: Dental Materials Guidance on Testing of Adhesion to Tooth Structure" at 14.8 MPa, which corresponds to a good dentine adhesion.

Example 8

Preparation of a Composite Cement Based on MA15-C5

In accordance with Table 3 given below, composite fixing cements were prepared on the basis of a dimethacrylate mixture with the polymerizable crown ether MA15-C5 (cement A), the monofunctional benzyl methacrylate (cement B, comparison example) and a mixture of MA15-05 with a phosphonic acid monomer (cement C) and also in each case a mixture of camphorquinone and p-N,N-dimethylaminobenzoic acid ethyl ester as photoinitiator using an "Exakt" roll mill (Exakt Apparatebau, Norderstedt). Corresponding testpieces were prepared from the materials, irradiated twice for 3 min with a dental light source (Spectramat®, Ivoclar Vivadent AG) and cured. The bending strength and bending E modulus were measured according to the ISO standard ISO-4049 (Dentistry—Polymer-based filling, restorative and luting materials).

TABLE 3

Composition of the acidic composite cements
(values in wt.-%)

| Component | Cement A | Cement B* | Cement C |
|---|---|---|---|
| Camphorquinone | 0.24 | 0.24 | 0.24 |
| p-N,N-dimethylaminobenzoic acid ethyl ester | 0.23 | 0.23 | 0.23 |
| UDMA[1] | 27.75 | 27.75 | 23.85 |
| Triethylene glycol dimethacrylate | 7.81 | 7.81 | 7.81 |
| Polymerizable crown ether MA15-C5 | 3.90 | — | 3.90 |
| Benzyl methacrylate | — | 3.90 | — |
| Phosphonic acid MA-154[2] | — | — | 3.90 |
| Aerosil ® OX-50 (Evonik Degus-sa)[3] | 41.34 | 41.34 | 41.34 |
| Ytterbium trifluoride (Rhone-Poulenc)[4] | 18.73 | 18.73 | 18.73 |

*Comparison example
[1]Addition product of 2 mol 2-hydroxyethyl methacrylate and 1 mol 2,2,4-trimethylhexamethylene diisocyanate
[2]2-[2-dihydroxyphosphoryl)-ethoxymethyl]-acrylic acid ethyl ester
[3]Silanized pyrogenic silicic acid with a BET surface area of 50 ± 15 m$^2$/g and an average primary particle size of 40 nm
[4]Particle size of 200 to 250 nm

TABLE 4

Composite cement properties

| Material property | Cement A | Cement B* | Cement C |
|---|---|---|---|
| Bending strength (MPa) after 24 h WI[1] | 109 | 109 | 111 |
| E modulus (MPa) after 24 h WI[1] | 5165 | 5200 | 5100 |

*Comparison example
[1]WI = water immersion of the testpieces at 37° C.

It can be seen from Table 4 that the cement A, based on polymerizable crown ether MA15-C5, and the cement C, based on the mixture of MA15-C5 and a phosphonic acid monomer, result in comparable mechanical properties in comparison with cement B (comparison example of conventional cement without crown ether and phosphonic acid) and thus there is no impairment by the polar crown ether monomer.

Example 9

Preparation of a Composite Based on MA15-C5

In accordance with Table 5 given below, composites were prepared on the basis of a dimethacrylate mixture and including the polymerizable crown ether MA15-C5 (composite A) or the monofunctional benzyl methacrylate (composite B, comparison example) and also a mixture of camphorquinone (CQ) and p-N,N-dimethylaminobenzoic acid ethyl ester (EMBO) as photoinitiator using an LPM 0.1 SP kneader (Linden, Marienheide). Corresponding test pieces were prepared from the materials, irradiated twice for 3 minutes with a dental light source (Spectramat®, Ivoclar Vivadent AG) and thus cured. The bending strength and bending E modulus (Table 6) were measured according to the ISO standard ISO-4049 (Dentistry—Polymer-based filling, restorative and luting materials).

TABLE 5

Composition of the filling composites
(values in wt.-%)

| Component | Composite A | Composite B* |
|---|---|---|
| Monomer resin[1] | 18.11 | 18.11 |
| Polymerizable crown ether MA15-C5 | yes | — |
| Benzyl methacrylate | — | yes |
| Glass filler GM27884 (Schott)[2] | 51.61 | 51.61 |
| Spherosil (Tokuyama Soda)[3] | 14.39 | 14.39 |
| Ytterbium trifluoride (Rhone-Poulenc)[4] | 14.89 | 14.89 |
| Aerosil ® OX-50 (Evonik Degussa)[5] | 1.00 | 1.00 |

*Comparison example
[1]Mixture of
38.00 wt.-% bis-GMA,
34.12 wt.-% UDMA,
17.07 wt.-% triethylene glycol dimethacrylate,
0.31 wt.-% CQ,
0.50 wt.-% EMBO and, as appropriate,
10.00 wt.-% MA15-C5 (composite A) or benzyl methacrylate (composite B)
[2]Silanized Ba—Al-borosilicate glass filler with an average particle size of 1.5 µm,
[3]SiO$_2$—ZrO$_2$ mixed oxide with an average primary particle size of 250 nm
[4]Particle size of 200 to 250 nm
[5]Silanized pyrogenic silicic acid with a BET surface area of 50 ± 15 m$^2$/g and an average primary particle size of 40 nm

TABLE 6

Filling composite properties

| Material property | Composite A | Composite B* |
|---|---|---|
| Bending strength (MPa) after 24 h WI[1] | 162 | 159 |
| Bending E modulus (GPa) after 24 h WI[1] | 13170 | 13890 |

*Comparison example
[1]WI = water immersion of the testpieces at 37° C.

It can be seen from Table 6 that the composite A, based on the polymerizable crown ether MA15-C5, results in comparable mechanical properties in comparison with composite B (comparative example of conventional composite without crown ether) and thus there is no impairment of the usual composite properties by the polar crown ether monomer.

What is claimed:

1. A dental material containing at least 0.05 wt.-% of at least one radically polymerizable macrocyclic polyether or radically polymerizable macrocyclic heteroanalogous polyether, wherein the radically polymerizable macrocyclic polyether or macrocyclic heteroanalogous polyether conforms to the general formula I MC-(SP-PG)n, where MC corresponds to a residue, substituted n times, of a crown ether or heteroanalogous crown ether of the general formula IIa

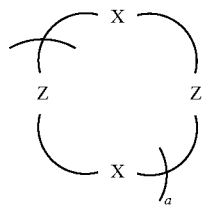

(IIa)

wherein
X is selected independently of each other in each case from O, S and $NR^1$, wherein $R^1$ stands independently of each other for H, the residue SP-PG or another organic residue, and wherein the X groups are O atoms, a combination of O atoms and S atoms, $NR^1$ groups or a combination of O atoms and $NR^1$ groups;
Z is selected independently of each other in each case from $C_1$-$C_4$ alkylene, $C_6$-$C_{10}$ arylene and $C_4$-$C_8$ cycloalkylene residues;
a is an integer from 3 to 10;
SP is independently of each other a linking group or is omitted,
PG is a radically polymerizable group, and
n is an integer from 1 to 8,
wherein SP-PG and/or PG is bonded to MC via at least one of the Z residues and for X=$NR^1$ additionally or exclusively via at least one N atom, and
further containing 20 to 75 wt.-% of at least one particulate filler and/or 5 to 70 wt.-% of solvent, in each case relative to the total weight of the dental material.

2. The dental material according to claim 1, in which the X groups are O atoms or a combination of O atoms and S atoms.

3. The dental material according to claim 2, in which (a+1−n) Z residues are ethylene residues and n Z residues are PG- and/or SP-PG-substituted $C_6$-$C_{10}$ arylene and/or $C_4$-$C_8$ cycloalkylene residues.

4. The dental material according to claim 1, in which the X groups are $NR^1$ groups or a combination of O atoms and $NR^1$ groups.

5. The dental material according to claim 4, in which $R^1$ in n $NR^1$ groups corresponds to a PG and/or SP-PG residue and all Z residues are ethylene residues.

6. The dental material according to claim 1, in which the radically polymerizable group PG is a vinyl, allyl and/or (meth)acryloyl group.

7. The dental material according to claim 1, in which the linking group SP conforms to the formula —$R^4$—$Z^1$—$R^5$—$Z^2$, where $Z^1$ and $Z^2$ are the same or different and in each case stand for —O—, —CO—O—, —O—CO—, —CO—NH—, —NH—CO—, —O—CO—NH— or —NH—CO—O— or one or both of $Z^1$ and $Z^2$ are absent and $R^4$ and $R^5$ are the same or different and in each case stand for a $C_1$-$C_{10}$ alkylene residue or one or both of $R^4$ and $R^5$ are absent.

8. The dental material according to claim 1, which is an adhesive, a coating material, a cement or a composite.

9. A dental material, which is an adhesive or a coating material and contains:
(i) 0.05 to 40 wt.-% of the at least one radically polymerizable macrocyclic polyether and/or macrocyclic heteroanalogous polyether,
wherein the radically polymerizable macrocyclic polyether or macrocyclic heteroanalogous polyether conforms to the general formula I MC-(SP-PG)n, where MC corresponds to a residue, substituted n times, of a crown ether or heteroanalogous crown ether of the general formula IIa

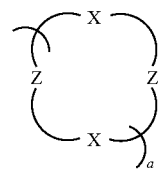

(IIa)

wherein
X is selected independently of each other in each case from O, S and $NR^1$, wherein $R^1$ stands independently of each other for H, the residue SP-PG or another organic residue, and wherein the X groups are O atoms, a combination of O atoms and S atoms, $NR^1$ groups or a combination of O atoms and $NR^1$ groups;
Z is selected independently of each other in each case from $C_1$-$C_4$ alkylene, $C_6$-$C_{10}$ arylene and $C_4$-$C_8$ cycloalkylene residues;
a is an integer from 3 to 10;
SP is independently of each other a linking group or is omitted,
PG is a radically polymerizable group, and
n is an integer from 1 to 8,
wherein SP-PG and/or PG is bonded to MC via at least one of the Z residues and for X=$NR^1$ additionally or exclusively via at least one N atom, and
further contains
(ii) 0.01 to 10 wt.-% of an initiator for the radical polymerization,
(iii) 0 to 80 wt.-% of at least one radically polymerizable monomer which is different from component (i),
(iv) 0 to 20 wt.-% of filler and
(v) 5 to 70 wt.-% of solvent,
in each case relative to the total weight of the dental material.

10. The dental material according to claim 8, which is a cement or a composite and contains:
(i) 0.05 to 40 wt.-% of the at least one radically polymerizable macrocyclic polyether and/or macrocyclic heteroanalogous polyether,
(ii) 0.01 to 10 wt.-% of an initiator for the radical polymerization,
(iii) 0 to 80 wt.-% of at least one radically polymerizable monomer which is different from component (i) and
(iv) 20 to 75 wt.-% of filler,
in each case relative to the total weight of the dental material.

11. The dental material according to claim 3, in which the n Z residues are PG- and/or SP-PG-substituted phenylene and/or cyclohexylene residues.

12. The dental material according to claim 9, in which the material contains (i) 1 to 30 wt.-% of the at least one radically polymerizable macrocyclic polyether and/or macrocyclic heteroanalogous polyether, (ii) 0.1 to 3.0 wt.-% of the initiator for the radical polymerization, (iii) 0 to 60 wt.-% of the at least one radically polymerizable monomer which is different from component (i), and (v) 5 to 70 wt.-% of solvent.

13. The dental material according to claim 10, in which the material contains (i) 1 to 30 wt.-% of the at least one radically polymerizable macrocyclic polyether and/or macrocyclic heteroanalogous polyether, (ii) 0.1 to 3.0 wt.-% of the initiator for the radical polymerization, and (iii) 0 to 60 wt.-% of the at least one radically polymerizable monomer which is different from component (i).

14. The dental material according to claim 9, in which the at least one radically polymerizable monomer which is different from component (i) comprises at least one acid group-containing adhesive monomer.

15. The dental material according to claim 14, in which the adhesive monomer is selected from the group consisting of phosphonic acid group-containing monomers, phosphoric acid group-containing monomers and sulphonic acid group-containing monomers.

16. The dental material according to claim 1, in which the filler has a particle size of 5 nm to 2,000 µm.

17. The dental material according to claim 15, in which the filler is selected from the group consisting of amorphous spherical materials based on oxides, nanoparticulate fillers, micro-fine fillers, minifillers and x-ray opaque fillers.

* * * * *